United States Patent [19]

Makovec et al.

[11] Patent Number: 4,870,097
[45] Date of Patent: Sep. 26, 1989

[54] PHARMACEUTICAL USE OF DERIVATIVES OF TRYPTOPHAN

[75] Inventors: Francesco Makovec; Rolando Chiste; Angelo L. Rovati, all of Monza, Italy

[73] Assignee: Rotta Research Laboratorium S.p.A., Milan, Italy

[21] Appl. No.: 217,116

[22] Filed: Jul. 11, 1988

Related U.S. Application Data

[62] Division of Ser. No. 893,555, Aug. 4, 1986, abandoned.

[30] Foreign Application Priority Data

Dec. 12, 1984 [IT] Italy .............................. 68241-A/84
Dec. 5, 1985 [WO] PCT Int'l Appl. ... PCT/EP85/00672

[51] Int. Cl.$^4$ ........................................... A61K 31/405
[52] U.S. Cl. ..................................... 514/419; 548/495
[58] Field of Search ......................................... 514/419

[56] References Cited

FOREIGN PATENT DOCUMENTS 0106281 6/1983 European Pat. Off. .
1352472 5/1974 United Kingdom .

OTHER PUBLICATIONS

Patricia L. Faris & Barry R. Komisaruk, "Evidence for the Neuropeptide Cholecstokin as an Antagonist of Opiate Analgesia", Sep. 28, 1982, Science, vol. 219, pp. 310-312.

Robert T. Jensen, Susanna W. Jones & Jerry D. Gardner "Structure-of N-Acyl Derivatives of Tryptophan that Function as a Specific Cholecystokinin Function Studies Receptor Antagonists", May 24, 1983, 1983 Elsevier Science Publishers B.V., pp. 269-277, Biochimica et Biophysica Acta 761 (1983).

"Reversing Opiate Tolerance: Proglumide Provides New Clue" American Pharmacy, vol. NS24, No. 8, Aug. 1984 508, pp. 20-21.

L. R. Watkins, I. B. Kinscheck, E. F. S. Kaufman, J. Miller, H. Frenk & D. J. Mayer, "Cholecystokinin Antagonists Selectively Potentiate Analgesia Induced by Endogenous Opiates" Brian Research, 327 (1985) 181-190.

Primary Examiner—David B. Springer
Attorney, Agent, or Firm—Sughrue, Mion, Zinn, Macpeak & Seas

[57] ABSTRACT

N-acylated derivatives of L-tryptophan of general formula (I),

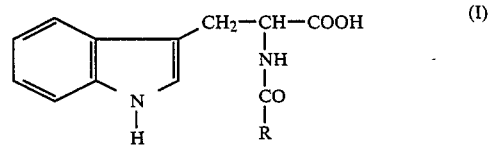

in which R is selected from the group consisting of: (a) a phenyl group, mono-substituted or di-substituted in the meta and para positions with halogens, linear or branched alkyl groups containing from 1 to 9 carbon atoms, the cyano group or the trifluoromethyl group, (b) a benzyloxy group, mono-substituted or di-substituted in the meta and para position with substituents selected from those indicated at (a), and (c) a benzydryloxy group. The derivatives are used in therapy, particularly for human pain relief, in the treatment of pathological conditions of the central nervous system and of pathological intestinal conditions.

4 Claims, No Drawings

PHARMACEUTICAL USE OF DERIVATIVES OF TRYPTOPHAN

This is a division of application Ser. No. 06/893,555 filed Aug. 4, 1986, abandoned.

The present invention relates to N-acylated derivatives of L-tryptophan which may be represented by the formula given below:

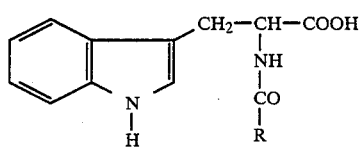

in which R is selected from the group consisting of:

(a) a phenyl group, mono-substituted or di-substituted in the meta and para positions with halogens, with linear of branched alkyl groups containing from 1 to 9 carbon atoms, with the cyano group or with the trifluoromethyl group, (b) a benzyloxy group, mono-substituted or di-substituted in the meta and para positions with substituents selected from those indicated at (a), and (c) a benzydryloxy group.

The subject of the present invention is a new therapeutic use of these N-acylated derivatives of L-tryptophan for use either alone or in association with analgesic-narcotic drugs in the treatment of pain of any etiology and intensity.

Several of the compounds of the present invention were previously disclosed by the applicants (see for example UK Pat. No. 1352472) for several of their interesting pharmacological activities, such as their anti-gastric-secretion activity and their protective action on the gastro-intestinal mucous membranes.

The applicants have now discovered that these N-acyl derivatives of tryptophan have an unexpected but extremely interesting therapeutic activity, that is, that of potentiating the analgesic activity of morphine and other analgesic-narcotic and non-narcotic drugs.

This potentiation in fact, in the first case, enables the posology of the opiates to be reduced thus limiting their multitude of well known undesirable side effects, without thereby reducing their therapeutic effectiveness and, in point of fact, considerably increasing their therapeutic indices.

These compounds may be used to re-establish the analgesic activity of opiate drugs when their pharmacological effect has declined as a result of the well known tolerance phenomenon, without the need to increase the therapeutic doses thereof. These favourable therapeutic characteristics could thus also serve to enable the gradual detoxification of subjects who have become addicted through the prolonged use of opiate drugs.

In the case of non-narcotic analgesics, benefit results from the protection of the gastric mucous membranes which are normally damaged by such products, in addition to the increased analgesic activity which is, in itself, very useful.

This potentiation of the activity of analgesic drugs may be related to the capacity of the compounds of the invention to block the hydrolytic degradation of enkephalins, endogenous physiological peptides having a powerful analgesic activity. This would give the enkephalins themselves a longer half-life and, by definitions, a greater activity.

Some of these compounds also have autonomous analgesic activities which could be used directly in pain relief.

The compounds of the invention also have considerable antagonistic activity towards cholecystokinin (CCK) in various experimental models both in vivo and in vitro. Thus they reduce CCK-induced contractions of the gall bladder in guinea pigs in vitro and in vivo they inhibit induced contractions of the colon in rabbits.

On the basis of the pharmacological characteristics one may also foresee their use in the treatment of psychic disturbances of various types which can, but need not, be imputed to reductions in the physiological neuron levels of the CCK or other bioactive polypeptides, or in the treatment of anorexia.

The method of preparation of the compounds of the invention consists of an acylation reaction under Schotten-Bauman conditions. Thus one mole of L-tryptophan is reacted with one mole of a suitable acyl chloride in the presence of two moles of base (generally sodium bicarbonate or hydroxide) at a temperature of between 0° and 10° C. for a period of between 1 hour and 24 hours.

After acidification, the compounds are isolated and purified by crystallisation.

The following examples are given better to illustrate the invention.

EXAMPLE 1 (SEE COMPOUND 1-TABLE A)

To a solution containing 20.4 g (0.1 moles) of L-tryptophan in 100 ml of 1N sodium hydroxide cooled to 5° C., there are added 100 ml of 1N sodium hydroxide and 18.9 g (0.1 moles) of p-fluorobenzyl chloroformate dissolved in 150 ml of ethyl acetate, simultaneously, under agitation and cooling, over a period of about 30 minutes. The mixture is left to react for twelve hours. The layers are separated and the slightly-alkaline aqueous phase is acidified;

N-p-fluorocarbobenzoxy-L-tryptophan is precipitated and separated by filtration. The crude compound is recrystallised from methano-$H_2O$ (1:1).

M.p.: 122°–4° C. TLC (see note in the table) Rf: 0.40 23.6 g obtained: Yield: 66%

All the compounds of the invention were made by the same method.

The compounds obtained are given in Table A together with several characteristics which identify them and the yields obtained and the solvents of crystallisation used.

The analgesic activity displayed by the compounds of the invention will now be illustrated by a series of pharmacological experiments arranged to show both their potentiation of the analgesic activity of opiates and the mechanism through which the potentiation is manifested.

TABLE A

N—acyl derivatives of L-tryptophan:

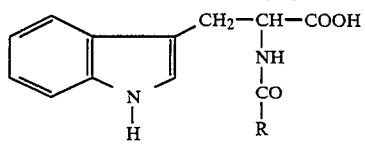

| Compounds | R | Melting Point (°C.) | Solvent of Crystallization | Rf(*) | Yield (%) | Formula |
|---|---|---|---|---|---|---|
| 1 | 4-fluoro-benzyloxy | 122–4 | MetOH/H$_2$O (1:1) | 0.40 | 66 | C$_{19}$H$_{17}$FN$_2$O$_4$ |
| 2 | 4-chloro-benzyloxy | 124–6 | MetOH/H$_2$O (7:3) | 0.45 | 88 | C$_{19}$H$_{17}$ClN$_2$O$_4$ |
| 3 | 4-bromo-benzyloxy | 141–2 | MetOH/H$_2$O (3:2) | 0.47 | 79 | C$_{19}$H$_{17}$BrN$_2$O$_4$ |
| 4 | 4-iodo-benzyloxy | 170–2 | MetOH/H$_2$O (2:1) | 0.51 | 80 | C$_{19}$H$_{17}$IN$_2$O$_4$ |
| 5 | 3-chloro-benzyloxy | 107–8 | EtOH/H$_2$O (1:1) | 0.48 | 84 | C$_{19}$H$_{17}$ClN$_2$O$_4$ |
| 6 | 3,4-dichloro-benzyloxy | 144–5 | MeOH/H$_2$O (1:1) | 0.51 | 56 | C$_{19}$H$_{16}$Cl$_2$N$_2$O$_4$ |
| 7 | 4-trifluoro-methyl-benzyloxy | 146–7 | EtOH/H$_2$O (1:1) | 0.40 | 77 | C$_{20}$H$_{17}$F$_3$N$_2$O$_4$ |
| 8 | 4-methyl-benzyloxy | 75–7 | EtOH/H$_2$O (1:1) | 0.41 | 77 | C$_{20}$H$_{20}$N$_2$O$_4$ |
| 9 | 4-ethyl-benzyloxy | 114–5 | EtOH/H$_2$O (7:3) | 0.42 | 78 | C$_{21}$H$_{22}$N$_2$O$_4$ |
| 10 | 3-chloro-4-methyl-benzyloxy | 132–3 | MetOH/H$_2$O (1:1) | 0.43 | 57 | C$_{20}$H$_{19}$ClN$_2$O$_4$ |
| 11 | 4-cyano-benzyloxy | 111–2 | MetOH/H$_2$O (2:1) | 0.40 | 82 | C$_{20}$H$_{17}$N$_3$O$_4$ |
| 12 | 4-chloro-phenyl | 148–50 | Benzene | 0.59 | 87 | C$_{18}$H$_{15}$ClN$_2$O$_3$ |
| 13 | 4-bromo-phenyl | 162–3 | Benzene | 0.62 | 84 | C$_{18}$H$_{15}$BrN$_2$O$_3$ |
| 14 | 4-fluoro-phenyl | 85–7 | EtOH/H$_2$O (6:5) | 0.57 | 86 | C$_{18}$H$_{15}$FN$_2$O$_3$ |
| 15 | 4-iodo-phenyl | 240–5 | EtOH/H$_2$O (3:1) | 0.68 | 92 | C$_{18}$H$_{15}$IN$_2$O$_3$ |
| 16 | 3-chloro-phenyl | 160–1 | Benzene | 0.64 | 73 | C$_{18}$H$_{15}$ClN$_2$O$_3$ |

(*)Note Eluent: isoamyl alcohol - acetone - H$_2$O (5:2:1)

| Compounds | R | Melting Point (°C.) | Solvent of Crystallization | Rf(*) | Yield (%) | Formula |
|---|---|---|---|---|---|---|
| 17 | 3,4-dichlo-rophenyl | 137–9 | Toluene | 0.70 | 89 | C$_{18}$H$_{14}$Cl$_2$N$_2$O$_3$ |
| 18 | 4-methyl-phenyl | 149–51 | H$_2$O/alcohol (1:1) | 0.55 | 88 | C$_{19}$H$_{18}$N$_2$O$_3$ |
| 19 | 4-ethyl-phenyl | 93–5 | Ligroin/Et.acet. (7:3) | 0.58 | 75 | C$_{20}$H$_{20}$N$_2$O$_3$ |
| 20 | 4-isopropyl-phenyl | 96–9 | Benzene | 0.59 | 75 | C$_{21}$H$_{22}$N$_2$O$_3$ |
| 21 | 3-methyl-phenyl | 108–10 | H$_2$O/alcohol (1:1) | 0.70 | 76 | C$_{19}$H$_{18}$N$_2$O$_3$ |
| 22 | 4-propyl-phenyl | 127–30 | C$_6$H$_6$/Ligroin (3:2) | 0.62 | 81 | C$_{21}$H$_{22}$N$_2$O$_3$ |
| 23 | 4-butyl-phenyl | 108–10 | Isopropyl ether | 0.65 | 67 | C$_{22}$H$_{24}$N$_2$O$_3$ |
| 24 | 4-isobutyl-phenyl | 190–1 | Isopropyl ether | 0.67 | 84 | C$_{22}$H$_{24}$N$_2$O$_3$ |
| 25 | 4-pentyl-phenyl | 127–30 | Isopropyl ether | 0.72 | 79 | C$_{23}$H$_{26}$N$_2$O$_3$ |
| 26 | 4-hexyl-phenyl | 128–31 | Isopropyl ether | 0.77 | 74 | C$_{24}$H$_{28}$N$_2$O$_3$ |
| 27 | 4-heptyl-phenyl | 112–5 | Ligroin/Et.acet. (3:2) | 0.79 | 68 | C$_{25}$H$_{30}$N$_2$O$_3$ |
| 28 | 4-nonyl-phenyl | 70–2(*) | H$_2$O | 0.82 | 47 | C$_{27}$H$_{33}$N$_2$O$_3$Na |
| 29 | 3,4-dimethyl-phenyl | 122–5 | Ligroin/Et.acet. (1:4) | 0.66 | 74 | C$_{20}$H$_{20}$N$_2$O$_3$ |
| 30 | 4-trifluoro-methyl-phenyl | 160–1 | Benzene | 0.54 | 78 | C$_{19}$H$_{15}$F$_3$N$_2$O$_3$ |
| 31 | 4-cyano-phenyl | 125–7 | H$_2$O/alcohol (3:2) | 0.52 | 87 | C$_{19}$H$_{15}$N$_3$O$_3$ |
| 32 | 3-cyano-phenyl | 84–90 | Toluene | 0.60 | 75 | C$_{19}$H$_{15}$N$_3$O$_3$ |
| 33 | benzhydryloxy | 92–5 | H$_2$O/alcohol (2:3) | 0.51 | 55 | C$_{25}$H$_{22}$N$_2$O$_4$ |

Note: (*) as the sodium salt

Experiment 1

Increase in the analgesic effect of analgesic-narcotic drugs in rats in the Tail Flick Test The method is that described by Harris et al. (J. Pharmacol. Exp. Ther. 143 (1964) 141–148).

Male rats are used which have a weight of about 150–200 g and which have not been fasting. A point is chosen on the tail and this is irradiated by a heat source (75° C.) and the time (in seconds) for which the animal remains without moving its tail is measured.

A maximum period of time under the heat source of 8 seconds is chosen after which the animal is, in any case, removed in order to avoid tissue damage. The measurement is effected before (controls) and after treatment with the drugs.

The administration of drugs of the invention is effected by i.p. (10 mg/kg) 10 minutes and immediately before administration of morphine (2 mg/kg). The percentage variation is calculated for each individual animal by the following formula:

$$\% \text{ variation} = \frac{\text{time after treatment} - \text{control time}}{8 - \text{control time}} \times 100$$

The measurements are carried out 10, 20, 30, 45, 60 and 90 minutes after treatment with the analgesics.

The results obtained are given in Table 1 which records the groups treated and the doses administered, the

TABLE 1

Potentiating activity of the indicated compounds of the invention an analgesia produced opiates in the "Tail-Flick" test

| Treatment | Times | | | | | | M(10'–90') ± S.E. | Potency ratio relative to morphine alone |
|---|---|---|---|---|---|---|---|---|
| | 10' | 20' | 30' | 45' | 60' | 90' | | |
| Controls | −10.2 ± 9.3 | 19.6 ± 4.1 | 46.4 ± 8.2 | −8.7 ± 13.5 | 18.2 ± 5.1 | 19.9 ± 8.3 | 14.2 ± 8.6 | |
| Morphine (M) | 10.8 ± 4.0 | 54.2 ± 17.0 | 46.6 ± 21.0 | 41.7 ± 16.0 | 32.0 ± 17.0 | −6.4 ± 10.0 | 29.8 ± 2.3 | 1 |

TABLE 1-continued

Potentiating activity of the indicated compounds of the invention an analgesia produced opiates in the "Tail-Flick" test

| Treatment | 10' | 20' | 30' | 45' | 60' | 90' | M(10'–90') ± S.E. | Potency ratio relative to morphine alone |
|---|---|---|---|---|---|---|---|---|
| M + *Comp.(C)-1 | 37.6 ± 12.9 | 89.2 ± 7.3 | 96.4 ± 3.5 | 82.6 ± 12.5 | 87.2 ± 7.8 | 40.6 ± 17.7 | 72.3 ± 26.1 | 2.43 |
| M + C-2 | 50.0 ± 14.9 | 25.0 ± 26.0 | 75.6 ± 17.6 | 23.7 ± 19.6 | 41.0 ± 20.3 | 43.6 ± 16.4 | 44.6 ± 20.0 | 1.50 |
| M + C-3 | 70.7 ± 19.7 | 90.3 ± 9.7 | 74.7 ± 16.9 | 86.2 ± 11.0 | 100.0 ± 0.0 | 53.7 ± 17.2 | 79.3 ± 16.4 | 2.66 |
| M + C-4 | 62.8 ± 22.8 | 76.9 ± 14.4 | 85.3 ± 13.9 | 56.4 ± 18.2 | 48.1 ± 16.9 | 19.4 ± 11.1 | 58.2 ± 23.3 | 1.95 |
| M + C-5 | 34.5 ± 13.3 | 53.0 ± 24.8 | 62.5 ± 16.6 | 50.5 ± 17.6 | 43.7 ± 10.1 | 52.2 ± 22.2 | 50.9 ± 10.3 | 1.71 |
| M + C-6 | 68.6 ± 20.4 | 78.0 ± 17.9 | 80.4 ± 19.6 | 84.5 ± 11.4 | 76.3 ± 13.8 | 71.9 ± 15.2 | 78.6 ± 5.7 | 2.57 |
| M + C-7 | 38.3 ± 13.7 | 34.4 ± 5.7 | 44.4 ± 14.8 | 48.3 ± 14.6 | 47.2 ± 16.9 | 47.9 ± 15.4 | 43.4 ± 5.8 | 1.45 |
| M + C-8 | 12.4 ± 4.9 | 38.4 ± 22.2 | 56.5 ± 20.3 | 48.0 ± 26.1 | 48.5 ± 21.5 | 54.4 ± 24.7 | 43.0 ± 16.3 | 1.44 |
| M + C-9 | 46.7 ± 14.7 | 62.2 ± 16.5 | 39.6 ± 15.7 | 86.9 ± 8.0 | 46.7 ± 20.4 | 40.8 ± 22.4 | 53.8 ± 18.1 | 1.80 |
| M + C-10 | 51.5 ± 48.9 | 58.3 ± 16.5 | 66.0 ± 14.1 | 56.9 ± 17.0 | 56.2 ± 23.5 | 34.2 ± 8.4 | 55.5 ± 11.0 | 1.86 |
| M + C-11 | 53.4 ± 13.5 | 80.0 ± 13.0 | 90.4 ± 9.6 | 84.9 ± 15.1 | 55.6 ± 18.3 | 50.9 ± 20.7 | 72.9 ± 17.2 | 2.45 |
| M + C-12 | 42.2 ± 19.4 | 50.5 ± 17.0 | 69.7 ± 19.8 | 68.9 ± 13.4 | 32.7 ± 20.1 | 16.3 ± 7.4 | 49.1 ± 20.9 | 1.65 |
| M + C-13 | 26.7 ± 5.6 | 72.6 ± 13.0 | 77.2 ± 10.0 | 86.2 ± 8.9 | 38.8 ± 11.3 | 12.6 ± 9.8 | 52.3 ± 30.3 | 1.75 |
| M + C-14 | 47.9 ± 21.0 | 90.2 ± 9.8 | 80.0 ± 12.5 | 67.7 ± 19.8 | 70.5 ± 18.1 | 61.5 ± 11.8 | 69.6 ± 14.7 | 2.33 |
| M + C-15 | 77.7 ± 13.8 | 81.7 ± 12.3 | 91.0 ± 9.0 | 89.0 ± 11.0 | 70.4 ± 17.2 | 60.3 ± 12.6 | 78.3 ± 11.6 | 2.63 |
| M + C-16 | 25.2 ± 21.8 | 39.5 ± 26.1 | 37.7 ± 22.9 | 33.1 ± 19.9 | 25.9 ± 18.1 | 9.7 ± 11.9 | 28.5 ± 10.9 | 0.96 |
| M + C-17 | 96.9 ± 4.1 | 100.0 ± 0.0 | 100.0 ± 0.0 | 50.3 ± 10.1 | 85.4 ± 11.5 | 29.6 ± 4.5 | 85.0 ± 27.7 | 2.85 |
| M + C-18 | 7.8 ± 16.1 | 14.9 ± 17.1 | 42.1 ± 18.3 | 26.6 ± 25.9 | 32.7 ± 25.9 | 41.1 ± 24.3 | 27.5 ± 14.0 | 0.93 |
| M + C-19 | 41.9 ± 12.8 | 43.9 ± 19.5 | 61.3 ± 18.1 | 49.4 ± 19.5 | 28.5 ± 17.0 | 14.4 ± 12.9 | 39.9 ± 15.0 | 1.34 |
| M + C-20 | 20.0 ± 12.8 | 33.1 ± 22.0 | 37.6 ± 18.9 | 37.5 ± 18.8 | 54.4 ± 19.3 | 33.2 ± 18.1 | 36.0 ± 11.0 | 1.21 |
| M + C-21 | 30.5 ± 19.7 | 89.0 ± 11.0 | 93.9 ± 6.1 | 85.9 ± 14.1 | 99.2 ± 0.8 | 56.3 ± 17.4 | 77.3 ± 23.8 | 2.59 |
| M + C-22 | 18.5 ± 5.3 | 39.3 ± 10.5 | 32.2 ± 7.9 | 37.1 ± 13.9 | 35.5 ± 10.0 | 24.5 ± 6.6 | 31.2 ± 8.2 | 1.05 |
| M + C-23 | 47.9 ± 15.7 | 50.3 ± 10.1 | 56.9 ± 20.6 | 67.2 ± 20.9 | 45.1 ± 16.3 | 36.1 ± 18.0 | 49.9 ± 11.1 | 1.67 |
| M + C-24 | 66.9 ± 14.8 | 61.9 ± 17.5 | 84.4 ± 11.6 | 69.1 ± 14.9 | 65.2 ± 11.4 | 32.7 ± 19.9 | 63.4 ± 16.9 | 2.13 |
| M + C-25 | 32.9 ± 17.3 | 63.7 ± 19.1 | 97.5 ± 2.5 | 100.0 ± 0.0 | 100.0 ± 0.0 | 82.9 ± 17.1 | 79.5 ± 26.8 | 2.67 |
| M + C-26 | 100.0 ± 0.0 | 87.6 ± 9.2 | 100.0 ± 0.0 | 100.0 ± 0.0 | 100.0 ± 0.0 | 84.5 ± 9.8 | 96.3 ± 7.3 | 3.2 |
| M + C-27 | 73.8 ± 18.1 | 95.2 ± 4.7 | 86.6 ± 9.0 | 87.7 ± 12.3 | 83.8 ± 9.9 | 88.4 ± 8.5 | 85.9 ± 7.0 | 2.88 |
| M + C-28 | 79.5 ± 12.7 | 100.0 ± 0.0 | 98.0 ± 2.0 | 100.0 ± 0.0 | 82.2 ± 17.8 | 78.8 ± 11.4 | 89.7 ± 10.6 | 3.01 |
| M + C-29 | 54.7 ± 14.1 | 62.6 ± 16.5 | 62.8 ± 17.5 | 65.9 ± 16.0 | 51.4 ± 12.7 | 52.5 ± 15.7 | 58.3 ± 6.1 | 1.96 |
| M + C-30 | 9.8 ± 10.5 | 45.6 ± 16.1 | 69.3 ± 22.2 | 62.3 ± 21.9 | 54.8 ± 17.6 | 24.7 ± 15.5 | 43.6 ± 21.8 | 1.46 |
| M + C-31 | 67.6 ± 16.1 | 66.3 ± 3.5 | 81.4 ± 14.7 | 73.4 ± 18.0 | 77.4 ± 10.3 | 21.3 ± 16.5 | 64.6 ± 22.0 | 2.17 |
| M + C-32 | 18.7 ± 6.7 | 60.7 ± 15.5 | 63.7 ± 16.3 | 63.7 ± 16.3 | 45.8 ± 16.1 | 22.8 ± 12.2 | 43.0 ± 14.9 | 1.44 |
| M + C-33 | 100.0 ± 0.0 | 87.6 ± 12.4 | 89.2 ± 10.8 | 97.0 ± 3.0 | 65.7 ± 21.4 | 58.1 ± 21.7 | 82.9 ± 17.1 | 2.78 | average percentage variations (calculated on groups of five animals) in the latency of the pain sensation, the average values calculated in the period 1–90 minutes (±S.E.) and the ratio of the potency of morphine administered alone and together with the compounds of the present invention.

From the data given in Table 1, it is seen that, at the tested dose (10 mg/kg i.p.) the products potentiate the activity of morphine up to as much as 3 times the activity of morphine alone for the most active products.

Experiment No. 2

Hot plate test

The method is that described by Eddy et al. (J. Pharmac. Exp. Ther. 107, 385 (1953)).

Groups of five male rats having a weight of about 150 g and which have not been fasting are used.

The animals are placed on a metal plate which is on the bottom of a transparent cylinder heated to 55°±1° C. by an azeotropic boiling mixture (1:1 acetone-ethyl formate). The time which passes between the moment at which the animal is placed on the hot plate and the moment at which it licks its feet or tries to jump out of the cylinder is defined as the reaction time. The control reaction time is measured 10 and 5 minutes before the administration of the drugs and 10, 20, 30, 45, 60, 90 minutes afterwards. The animals are left on the plate for a maximum period of 30 seconds.

The response to the administration of the product is considered positive if at least a doubling of the normal reaction time is seen. The results obtained are given in Table 2 which records the groups treated, the dose administered and the stay times on the plate expressed as the number of positive responses over the number treated.

TABLE 2

Potentiating activity of the compounds of the invention on the activity of analgesic drugs in the hot plate test

| TREATMENT | Dosage mg/kg i.p. | 10' | 20' | 30' | 45' | 60' | Positive Total X/25 |
|---|---|---|---|---|---|---|---|
| Propoxyphene (Prop) | 15 | 2/5 | 2/5 | 3/5 | 3/5 | 1/5 | 11 |
| Prop. + Compound 26 | 15 + 1 (C. 26) | 2/5 | 3/5 | 4/5 | 3/5 | 3/5 | 15 |
| " | 15 + 2.5 (C. 26) | 3/5 | 5/5 | 5/5 | 4/5 | 3/5 | 20 |
| " | 15 + 5.0 (C. 26) | 4/5 | 5/5 | 5/5 | 5/5 | 5/5 | 24 |
| Oxyphenylbutazone (Oxy) | 50 | 2/5 | 1/5 | 2/5 | 2/5 | 0/5 | 7 |
| Oxy + Compound 33 | 50 + 5 (C. 33) | 3/5 | 4/5 | 4/5 | 4/5 | 3/5 | 17 |
| " | 50 + 10 (C. 33) | 3/5 | 5/5 | 5/5 | 5/5 | 3/5 | 21 |
| " | 50 + 20 (C. 33) | 4/5 | 5/5 | 5/5 | 4/5 | 4/5 | 22 |
| Acetylsalicylic acid (Asa) | 100 | 1/5 | 2/5 | 2/5 | 2/5 | 0/5 | 7 |
| Asa + Compound 26 | 100 + 5 (C. 26) | 3/5 | 2/5 | 4/5 | 4/5 | 2/5 | 15 |

TABLE 2-continued

Potentiating activity of the compounds of the invention on the activity of analgesic drugs in the hot plate test

| TREATMENT | Dosage mg/kg i.p. | 10' | 20' | 30' | 45' | 60' | Positive Total X/25 |
|---|---|---|---|---|---|---|---|
| " | 100 + 10 (C. 26) | 5/5 | 4/5 | 5/5 | 4/5 | 3/5 | 21 |
| " | 100 + 20 (C. 26) | 4/5 | 5/5 | 5/5 | 5/5 | 4/5 | 23 |

From the results given in the Table it may be seen that even 2.5 mg/kg i.p. doses of the compound 26 can at least double the analgesic activity of propoxyphene. At doses of 5 mg/kg i.p. there is, in practice, a maximum effect.

In order to increase the analgesic activity of non-narcotic drugs, higher doses of the drugs of the invention are needed and the significance is generally comparable at the higher doses.

Experiment No. 3

Influence of several of the compounds of the invention on the analgesic activity of endogenous opiates released under transcutaneous shock in rats measured by the Tail Flick Test The method is that described by Lewis et al. (J. Neurosc. 1, 358 (1981). Male rats having a weight of about 200 g, which have not been fasting, are used.

The animals are stressed by the application to the front leg of a 60 Hz-2.5 mA current in pulses of a duration of one second every five seconds for 20 minutes.

This stress regime causes the release of endogenous opiates. Immediately after the electrical stimulation the animals are subjected to the Tail Flick Test at times indicated in the Table.

From the data given in the Table it is seen that, even at 0.5 mg/kg, several of the compounds of the invention can increase the analgesic effect of endogenous enkephalins, generally to a highly significant extent; this increase is dose-dependent, the effect in fact increasing both in intensity and duration in dependence on the dose.

Experiment No. 4

Potentiation of the analgesic activities of enkephalins induced by several of the compounds of the invention In order to check one of the possible mechanisms for the action of the compounds of the invention, that is, their possible inhibition of the enzymatic degradation of endogenous enkephalins, the following experiment was carried out:

A cannula was implanted in the right lateral ventricle of male rats having a weight of 150–200 g (groups of five animals were used) in order to allow the intracerebroventricular (i.c.v.) administration of drugs according to the method of Noble et al (Life Science 6, (1970) 281–291).

The animals were subsequently treated (i.c.v.) with 3 μg of D-ala-methionine-enkephalinamide (DALA) immediately after an injection (i.c.v.) of the compounds

TABLE 3

Average latency (in sec.) determined by the Tail Flick Test as different times (minutes) after the electric shock (average values for groups of 5 animals ± E.S.)

| TREATMENT | Doses mg/kg i.v. | Times | | |
|---|---|---|---|---|
| | | 5' | 10' | 15' |
| A: Controls | — | 2.88 ± 0.11 | 3.0 ± 0.29 | 2.70 ± 0.27 |
| B: Controls stressed | — | 5.16 ± 0.23 | 3.98 ± 0.203 | 3.10 ± 0.19 |
| t verso A | | 8.74 (*) | 2.54 (*) | 1.07 |
| C: Compound 26 | | | | |
| + stress | 0.5 | 6.62 ± 0.72 | 6.1 ± 0.61 | 5.52 ± 0.9 |
| t verso A | | 5.091 (*) | 4.47 (*) | 2.95 (*) |
| t verso B | | 1.91 | 3.27 (*) | 2.63 (*) |
| D: Compound 26 | | | | |
| + stress | 2 | 11.0 ± 0.65 | 9.28 ± 0.78 | 6.84 ± 0.73 |
| t verso A | | 12.1 (*) | 7.43 (*) | 5.21 (***) |
| t verso B | | 8.36 (*) | 6.56 (*) | 4.92 (**) |
| E: Compound 33 | | | | |
| + stress | 0.5 | 6.68 ± 0.53 | 6.58 ± 0.46 | 5.3 ± 0.56 |
| t verso A | | 7.02 (*) | 6.32 (*) | 4.1 (**) |
| t verso B | | 2.63 (*) | 5.11 (*) | 3.72 () |
| F: Compound 33 | | | | |
| + stress | 2 | 9.92 ± 0.92 | 8.1 ± 1.0 | 6.51 ± 0.48 |
| t verso A | | 7.54 (*) | 4.83 () | 6.77 (***) |
| t verso B | | 4.98 () | 4.02 () | 6.56 (**) |

Note:
(*) $P < 0.05$
(**) $P < 0.01$
(***) $P < 0.001$

The compounds are administered i.v. immediately before the electric shock at doses indicated in Table No. 3.

under study at the doses given in Table 4. Analgesia was tested for by the Tail Flick method already mentioned, at the times

TABLE 4

Increase in the analgesic activity of DALA induced by several compounds of the invention determined by the Tail Flick test in rats.

| GROUP | TREAT-MENT | TIMES DOSES mg/kg (ICV) | 10' | 20' | 30' | 45' | 60' | AVERAGE | Student's t |
|---|---|---|---|---|---|---|---|---|---|
| A | PHYSIO-LOGICAL | — | 1.34 ± 1.05 | 1.88 ± 2.61 | 3.28 ± 2.58 | 1.72 ± 2.69 | −1.89 ± 3.66 | 1.26 ± 0.85 | — |
| B | DALA (D) | 10 | 35.42 ± 10.62 | 47.04 ± 7.99 | 30.74 ± 15.41 | 26.58 ± 8.14 | 15.48 ± 5.59 | 31.05 ± 5.18 | To A: 5.18 (***) |
| C | DALA + Compound 26 | 10(D) + 0.001 | 62.44 ± 12.87 | 73.94 ± 9.84 | 67.94 ± 11.64 | 40.38 ± 7.06 | 34.06 ± 5.38 | 55.75 ± 7.84 | To A: 6.90 (***) Verso DALA: 2.63 (*) |
| D | DALA + Compound 26 | 10(D) ± 0.01 | 80.54 ± 13.48 | 82.66 ± 15.76 | 70.42 ± 15.90 | 45.9 ± 14.15 | 68.9 ± 13.17 | 69.68 ± 6.53 | To A: 10.38 (*) To DALA: 4.63 () |
| E | DALA + Compound 33 | 10(D) + 0.001 | 64.12 ± 22.02 | 77.56 ± 13.96 | 72.7 ± 14.93 | 45.76 ± 12.14 | 57.38 ± 13.92 | 63.50 ± 5.63 | To A: 10.92 (*) Verso DALA: 4.23 () |
| F | DALA + Compound 33 | 10(D) + 0.01 | 81.48 ± 14.60 | 100.00 ± 0.0 | 80.22 ± 4.92 | 59.24 ± 10.56 | 55.88 ± 8.19 | 75.36 ± 8.08 | To: A 9.11 (*) To DALA: 4.61 () |

Note:
(*) $P < 0.05$
(**) $P < 0.01$
(***) $P < 0.001$ given in the Table.

From the data given, the potentiating action of the compounds being tested on the analgesic effect of the enkephalinamide (DALA) both in intensity and duration can be seen.

This activity, which is highly significant at doses of 0.001 g/kg of proglumide, is probably relateds to an inhibiting activity of an enzyme (or enzymes) responsible for the metabolism of the enkephalins.

Experiment No. 5

Antagonism of several products which are the subject of the invention to the development of tolerance in rats to the repeated administration of morphine HCl Several of the compounds of the invention were examined to determine any capacity to antagonise the development of tolerance induced by morphine. Groups of six male rats having a weight of about 200–250 were used.

At intervals of 24 hours from the first treatment (time 0), each animal (except for the control group treated with a physiological solution) received 3 mg/kg of morphine hydrochloride i.p. together with 3 mg/kg i.p. of the compounds indicated (with the exception of the group treated solely with morphine).

The determination of the threshold for the pain stimulus was effected at 15', 30', 45' and 60' intervals from the treatment by the "tail flick" test.

The data given in Table no. 5 relate to the average

TABLE 5

Antagonism of several products of the invention to the development of induced tolerance in rats to the repeated administration of morphine HCl

| TREAT-MENT | DOSES | TIME (Day) 0 | 1 | 2 | 3 | 4 | 5 | 6 | 7 | Area subtended (1) (Effect-Day) | Area 1 Area Mor-phine |
|---|---|---|---|---|---|---|---|---|---|---|---|
| Control (Group A) | — | −0.73 ± 4.1 | 0.86 ± 1.04 | 5.43 ± 1.18 | 1.09 ± 1.90 | 3.97 ± 1.00 | 1.47 ± 1.58 | 1.08 ± 3.12 | −0.77 ± 1.08 | 18.4 | 0.13 |
| | | % Effect = −0.097 Day + 1.89 (r = 0.11 t = 0.27) | | | | | | | | | |
| Morphine (Group B) | 3 mg/kg (M) | 35.83 ± 14.0 15.6 | 37.43 ± 18.3 | 30.33 ± 10.6 | 16.06 ± 11.5 | 22.46 ± 2.9 | 9.63 ± 6.7 | 7.28 ± 2.3 | 1.95 ± | 140.3 | 1 |
| | | % Effect = −5.34 Day + 38.72 (r = 0.96 t = 8.39 (***)) | | | | | | | | | |
| Compound 26 (Group C) | 3 mg/kg +(M) | 74.14 ± 5.08 | 45.73 ± 9.07 | 59.5 ± 8.57 | 51.52 ± 5.18 | 43.40 ± 7.95 | 37.60 ± 9.87 | 21.43 ± 12.0 | 29.75 ± 6.96 | 366.7 | 2.61 |
| | | % Effect = −6.02 Day + 66.5 (r = 0.88 t = 4.53(**)) | | | | | | | | | |
| Compound 33 (Group D) | 3 mg/kg +(M) | 50.12 ± 6.1 | 67.02 ± 19.9 | 51.47 ± 11.9 | 34.92 ± 9.8 | 67.3 ± 11.4 | 61.08 ± 20.5 | 20.02 ± 6.7 | 10.33 ± 3.8 | 382.1 | 2.72 |
| | | % Effect = −5.38 Day + 64.12 (r = 0.61 t = 1.89)) | | | | | | | | | |
| Compound 1 (Group E) | 3 mg/kg +(M) | 44.25 ± 19.00 | 69.33 ± 17.39 | 69.21 ± 18.18 | 54.03 ± 16.04 | 21.91 ± 3.35 | 33.35 ± 10.69 | 36.44 ± 20.92 | 16.1 ± 5.98 | 342.6 | 2.44 |
| | | % Effect = − 5.97 Day + 63.96 (r = 0.73 t = 2.62 (*)) | | | | | | | | | |

Note:
(*) $P < 0.05$
(**) $P < 0.01$
(***) $P < 0.001$
r = coefficient of correlation values for these four determinations and indicate the percentage variations in the latency time (appearance of pain) before and after the treatment with the drugs.

From the data given in the table, and from the calculated straight lines of regression, it can be seen that, from the third treatment up to the end of the experiment, the compounds of the invention subjected to this test are more active than the group treated solely with morphine.

Furthermore, after the fifth treatment, the morphine group already is no longer significantly different from the control group while the groups C, D and E maintain their activities to a significant extent compared with the controls up to the last treatment on the seventh day.

From the calculation of the straight lines of regression it may also be seen that while the activity for the morphine group falls to 0 on the sixth day of treatment, the inactive level is reached on about the eleventh day (extrapulated value) for the groups C, D and E and, furthermore, the dose of 3 mg/kg/day for the compounds tested resulted, on average, in an increase of about 2.5 times the analgesic power of morphine.

The anti-CCK activity and the anti-spastic activity of the compounds of the invention will now be illustrated

Anti-CCK activity on guinea pig gall bladders "in vitro"

A longitudinal strip of guinea pig gall bladder is placed in a bath of Krebs for isolated organs at a temperature of 32° C. and oxygenated continuously with an oxygen-$CO_2$ mixture (95-5 V/V).

TABLE 6

Anti CCK-8 activity concentration used in 10 ng/ml of the compounds of the invention on the guinea pig gall bladder in vitro expressed as the ED50 in mcg/ml

| COMPOUND | ACTIVITY ED50 (mcg/ml) | COMPOUND | ACTIVITY ED50 (mcg/ml) |
|---|---|---|---|
| 1 | 59.9 | 17 | 398.0 |
| 2 | 13.5 | 18 | IN |
| 3 | 33.6 | 19 | 135.2 |
| 4 | 48.2 | 20 | 17.9 |
| 5 | 23.2 | 21 | IN |
| 6 | 16.1 | 22 | 25.7 |
| 7 | 108.7 | 23 | 74.0 |
| 8 | 114.3 | 24 | 327.7 |
| 9 | 125.4 | 25 | 103.8 |
| 10 | 88.5 | 26 | 152.1 |
| 11 | 34.3 | 27 | 148.5 |
| 12 | 206.0 | 28 | 18.9 |
| 13 | 158.0 | 29 | IN |
| 14 | 233.2 | 30 | IN |
| 15 | IN | 31 | IN |
| 16 | 197.5 | 32 | IN |
| | | 33 | 76.3 |

Note: IN = inactive up to 400 mcg/ml

The asymmetric contractions are detected by means of a force transducer and recorded.

The gall bladder is contracted with the use of a CCK-8 solution at a concentration of 10 ng/ml; the antagonistic activity of the compounds of the invention towards the contracting effect of the CCK is determined with the use of different concentrations, the ED50 value, that is the concentration of the compound in mcg/ml capable of antagonising 50% of the contracting effect of the CCK, being determined.

The results obtained are set out in the following table which gives the compounds tested and the ED50 values which are calculated by the method of regression on a test of at least three experiments for each compound studied.

From the data given in the table it is seen that the compounds claimed antagonise 50% of the activity of CCK-8 at a concentration which, for the most active compounds, is very low (10–20 mcg/ml).

By virtue of this anti-CCK activity, the compounds of the invention display an anti-spastic activity with a very specific mechanism useable to advantage in altered physiological conditions in which there is interproduction of cholecystokinin.

Such a situation is reproduced by the following experiment.

The abdomen of an anaesthetised rabbit is cut open to expose the transverse colon. A balloon full of water is inserted at the point established and connected to a pressure transducer by means of a polyethylene cannula filled with $H_2O$.

The optimum sensitivity in relation to the physiological contractions is fixed and the products are administered through the femoral veins. Contractions are induced by the administration of 100 ng/kg of CCK.

The activities of the products of the invention are given in Table no. 7.

TABLE 7

Antispastic activity in the colon of rabbits stimulated with CCK-8.

| COMPOUNDS | DOSES (mg/kg iv) | EXPERIMENT 1 | EXPERIMENT 2 | EXPERIMENT 3 | ED50 (mg/kg iv) n = coefficient of correlation |
|---|---|---|---|---|---|
| 2 | 1 | −10.9 | −16.8 | −38.8 | ED50 = 4.67 |
|  | 3 | −31.4 | −56.6 | −41.5 | r = 0.921 |
|  | 10 | −85.9 | −74.4 | −90.2 | t = 6.25 (***) |
| 20 | 0.3 | — | — | −12.8 |  |
|  | 1 | −30.8 | −44.2 | −34.7 | ED50 = 3.41 |
|  | 3 | −36.0 | −60.3 | −59.0 | r = 0.913 |
|  | 10 | −82.5 | −100.0 | — | t = 5.92 (***) |

(***) $P < 0.001$

The data given indicate that several of the compounds tested which are the subject of the present invention, as already shown for the gall bladder, also antagonise interstinal contractions induced by CCK administered in large doses (100 ng/kg).

The antispastic activity is manifested at very low doses, of between 1 and 5 mg/kg, for the best of the compounds used.

The experimental data given above appear to provide ample basis for considering the use of the drugs of the invention in association with morphine or other analgesic drugs (narcotic or otherwise) as a considerable therapeutic innovation capable of providing the doctor with components of pre-eminent interest for the treatment of pain of any etiology. This treatment seems to be particularly indicated in the case of prolonged administrations of opiates where there is a great need for the drug not to cause habituation or at least for this to be kept within acceptable limits. Furthermore their possible use in the detoxication of patients who have become addicted through the prolonged use of opiate drugs is of enormous therapeutic and social interest.

The experimental data given above also show the utility of these compounds in the treatment of various pathological conditions of the intestinal system, particularly in the treatment of biliary diskinesia and irritable colon particularly when these pathological forms are related to the hyperproduction of cholecystokinin.

Some of these compounds have also been shown to have autonomous analgesic activities which may be used to advantage in the treatment of pathological conditions with an algic component.

One may also keep in mind the powerful anti-CCK activity exhibited by many of the compounds in question, a favourable therapeutic use in the treatment of anorexia or in some pathological conditions of the SNC linked to embalances in the physiological neuron levels of the CCK or other bio-active peptides.

We claim:

1. A process for relieving pain in a human which comprises administering to said human a pain-relieving effective amount of a pharmaceutically-active N-acylated derivative of L-tryptophan of general formula:

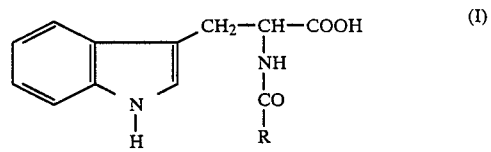

in which R is selected from the group of:
 (a) a phenyl group, mono-substituted or di-substituted in the meta and para positions with halogens, with linear or branched alkyl groups containing from 1 to 9 carbon atoms, with the cyano groups or with the trifluoromethyl group,
 (b) a benzyloxy group, mono-substituted or di-substituted in the meta and para positions with substituents selected form those indicated at (a), and
 (c) a benzydryloxy group, or a pharmaceutically acceptable salt thereof.

2. The process of claim 1 wherein said derivative of L-trypthophan is administered in association with at least one of a non-narcotic analgesic drug and an analgesive-narcotic drug.

3. The process of claim 2 wherein said compound of the formula (I) is present in an amount effected to potentiate the activity of said at least one non-narcotic analgesic and analgesic-narcotic drug.

4. A process for treating a pathological condition of the central nervous system which comprises administering to a patient a pathological central nervous system-treating effective amount of a pharmaceutically-active N-acylated derivative of L-tryptophane of general formula:

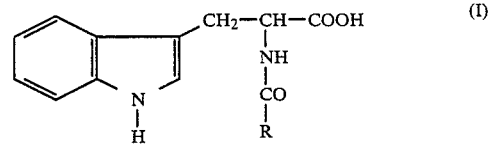

in which R is selected from the group consisting of:
 (a) a phenyl group, mono-substituted or di-substituted in the meta and para positions with halogens, with linear or branched alkyl groups containing from 1 to 9 carbon atoms, with the cyano group or with the trifluoromethyl group,
 (b) a benzyloxy group, mono-substituted or di-substituted in the meta and para positions with substituents selected from those indicated at (a), and
 (c) a benzydryloxy group, or a pharmaceutically acceptable salt thereof.

* * * * *